(12) United States Patent
Kim et al.

(10) Patent No.: US 6,449,336 B2
(45) Date of Patent: Sep. 10, 2002

(54) MULTI-SOURCE INTENSITY-MODULATED RADIATION BEAM DELIVERY SYSTEM AND METHOD

(76) Inventors: Siyong Kim, 3627 NW. 64th La., Gainesville, FL (US) 32653; Jatinder Palta, 2224 NW. 135th Tr., Gainesville, FL (US) 32606

( * ) Notice: Subject to any disclaimer, the term of this patent is extended or adjusted under 35 U.S.C. 154(b) by 0 days.

(21) Appl. No.: 09/859,813

(22) Filed: May 18, 2001

Related U.S. Application Data

(60) Provisional application No. 60/205,462, filed on May 19, 2000.

(51) Int. Cl.$^7$ .................................................. A61N 5/10
(52) U.S. Cl. .......................................................... 378/65
(58) Field of Search ............................................ 378/65

(56) References Cited

U.S. PATENT DOCUMENTS 5,802,136 A * 9/1998 Carol .......................... 378/65

* cited by examiner

Primary Examiner—Craig E. Church
(74) Attorney, Agent, or Firm—Miles & Stockbridge; Dennis P. Clarke

(57) ABSTRACT

A technique for Intensity-modulated radiation therapy (IMRT), an advanced form of external beam irradiation that is commonly referred as three-dimensional conformal radiation therapy (3DCRT), uses an array of radiation sources disposed within cells of a two-dimensional (2D) grid of radiation blocking walls. The intensity of radiation applied to a patient from any individual source is modulated dependent on local properties of a target, such as characteristics or dimensions of that portion of a tumor subject to radiation from a given source at a given time. In particular, each source is individually moved toward or away from the patient depending on the local (i.e., local to that source) properties of the target.

24 Claims, 4 Drawing Sheets

MULTI-SOURCE INTENSITY-MODULATED RADIATION BEAM DELIVERY SYSTEM AND METHOD

CROSS REFERENCE TO RELATED APPLICATION

The subject matter of this invention is related to Provisional Application Ser. No. 60/205,462, filed May 19, 2000. The subject matter of said application is hereby incorporated by reference.

BACKGROUND OF THE INVENTION

The field of the invention is a system and method for optimizing intensity-modulated radiation therapy (IMRT) delivery systems.

Radiation emitting devices are generally known and used, for instance, as radiation therapy devices for the treatment of patients. A radiation therapy device generally includes a gantry that can be swiveled around a horizontal axis of rotation in the course of a therapeutic treatment. A linear accelerator is, e.g., located in the gantry for generating a high-energy radiation beam for therapy. During treatment, this radiation beam is trained on a zone of a patient lying in the isocenter of the gantry rotation.

The point of such therapy is to concentrate radiation on tumors or other target zones, but minimize radiation dosages applied to adjacent healthy tissue, especially certain parts of the body (e.g., the optic nerve) that are more sensitive to radiation. A radiation source directs radiation towards the target zone. By moving the radiation source along an arc over a period of time, the radiation is on the target during the entire movement along the arc. However, healthy tissue adjacent the tumor (such as between the tumor and source, and tissue past the tumor along the beam path) receive radiation for only a small portion of the time, different sections of healthy tissue being in the radiation path at different places along the arc. Additionally, the patient is moved (usually rotated about a vertical axis) to achieve the same effect (i.e., radiation stays on the target during the entire treatment time, but healthy tissue is only exposed for a small fraction of the treatment time). Thus, the total radiation applied to the target may achieve the desired result, but the reduced radiation applied to adjacent tissue avoids or minimizes damage to the healthy tissues.

An important factor in such radiation treatment is maintaining the beam from the radiation source on the target zone. Precise positioning of the radiation source relative to the patient is thus required. The time of treatment affects the accuracy of the beam. A longer treatment time increases the chances that the patient or portion of the patient will move. Therefore, a shorter period of treatment is generally preferable because the chances of movement occurring is reduced.

To control the radiation emitted toward an object, a beam shielding device, such as a plate arrangement or a collimator, is typically provided in the trajectory of the radiation beam between the radiation source and the object. An example of a plate arrangement is a set of, e.g., four plates that can be used to define an opening for the radiation beam. A collimator is a beam-shielding device that could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam-shielding device defines a field on the object to which a prescribed amount of radiation is to be delivered. The usual treatment field shape results in a three-dimensional treatment volume that includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist, a doctor specializing in cancer and its treatment. The prescription is a definition of, for example, a particular volume and the level of radiation permitted to be delivered to that volume. A therapist, however, normally carries out actual operation of the radiation equipment. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

Modern day radiation therapy of, e.g., tumors has two goals: eradication of the tumor and avoidance of damage to healthy tissue and organs present near the tumor. It is known that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surfaces of the tumor, while minimizing the dose of radiation to surrounding healthy tissue or adjacent healthy organs.

Conformal radiation therapy has been traditionally approached through a range of techniques, and typically uses a linear accelerator ("LINAC") as the source of the radiation beam used to treat the tumor. The linear accelerator typically has a radiation beam source that is rotated about the patient and directs the radiation beam toward the tumor to be treated. The beam intensity of the radiation beam is a predetermined, constant beam intensity.

Multileaf collimators, which have multiple leaf, or finger, projections which can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Intensity modulated treatment is a specialized technique for radiation treatment. Usually, the beam-shielding device in intensity modulated treatment includes either (1) two pairs of opposing jaws or (2) a pair of jaws and a pair of opposing sets of multi-leaf collimator leaves. One pair of these jaws or the pair of multi-leaf collimator leaves move in the same direction at different speeds. This creates a sweeping opening for the radiation beam. Because the jaws (or leaves) are traveling at different speeds, the opening varies in size during the sweeping. Usually, elaborate speed control and thick jaws (or leaves) are needed for intensity modulated treatment. The speed control is needed for accurately defining the changing opening size. The thick jaws (or leaves) are needed because of a concern with radiation leakage. For example, due to the sweeping treatment, approximately three times the regular amount of radiation dose is needed to treat an area on a patient. Therefore, the radiation leakage for intensity modulated treatment is approximately three times greater than regular leakage. For example, a regular treatment of 100 monitor units (MU) of radiation results in approximately 0.1 MU of radiation leakage. With an intensity modulated treatment for the same field, 300 MU of radiation is required and results in 0.3 MU of radiation leakage.

Intensity modulated treatment usually utilizes a multi-leaf collimator. The multi-leaf collimator can be in addition to the jaws, replace a pair of jaws, or replace all of the jaws. This collimator is typically rotated around the patient during the radiation treatment to provide more accurate radiation coverage. The leaves in the collimator each have a motor and two sensors. The sensors monitor the position of each of the leaves. Unfortunately, standard multi-leaf collimators usually have radiation leakage of approximately 0.5% to 1.5%. When multi-leaf collimators are used with intensity modulated treatment, the deposited radiation leakage increases due to the required increase in radiation dose. This is an unnecessary exposure to healthy tissue.

As noted above, the delivery of radiation by a radiation therapy device is prescribed and approved by an oncologist but actual operation of the radiation equipment is normally done by a therapist. When the therapist administers delivery of the radiation as prescribed by the oncologist, the radiation-emitting device is programmed to deliver that specific treatment. When programming the treatment, the therapist has to take into consideration the actual radiation output and has to adjust the dose delivery based on the plate arrangement opening to achieve the prescribed radiation treatment at the target depth in the patient.

This adjustment can be made according to known calculations, but the therapist normally has to do them manually, which can lead to errors. In the context of radiation therapy, a miscalculation can lead to either a dose that is too low and is ineffective, or that is too high and dangerous.

Intensity-modulated radiation therapy (IMRT) is an advanced form of external beam irradiation that is often referred as three-dimensional conformal radiation therapy (3DCRT). It utilizes variable beam intensities across the irradiated volume that has been determined using computer optimization techniques. IMRT has the capability of generating concave dose distribution and of providing specific sparing of sensitive normal structures within complex treatment geometries. It represents the most significant technical advancement in radiation therapy since the advent of the medical linear accelerator.

Current IMRT delivery system consists of either using a physical compensation filter made of non-uniform thickness or a multi-leaf collimator (MLC) to obtain variable intensities.

In the case of MLC, a gap formed by each pair of opposing MLC leaves is swept across the target volume under computer control with the radiation beam 'ON' to produce the desired radiation intensity profile. Treatment times for IMRT can be very long because only a small part of the field is treated at a time in the case of MLC and a large amount of radiation intensity is absorbed in filter material in the case of a physical compensating filter. In IMRT it is not uncommon to have sharp gradients of dose distribution between target (or critical organ) and its surrounding region. A small amount of patient movement can produce large errors in dose delivery to target (or critical organ). Since there are more opportunities for a patient to move where treatment times are extended, it is always desirable to reduce treatment times as much as possible. Moreover, long radiation exposures result in higher doses outside the prescribed field due to radiation leakage from the treatment machine which is very difficult, if not impossible, to avoid. Accordingly, the focus of much current research in IMRT is to minimize the radiation 'ON' time by optimizing the leaf-sequencing algorithm.

Apart from various LINAC systems, and decades ago, Dr. Lars Leksell and others developed a radiation treatment device that is called the GAMMA KNIFE. The device consists of a hemispheric arrangement containing numerous Cobalt-60 sources. The radiation from each of these sources is collimated and mechanically fixed, with great accuracy, on a focal point at the center of the hemisphere. When a patient has a suitable lesion for treatment (such as an intracranial arteriovenous malformation), it may be precisely localized with another device called a stereotactic frame. Using the stereotactic apparatus, the intracranial target is positioned at the focal point of the GAMMA KNIFE. Since each of the numerous radiation pathways is through a different area of the brain, the amount of radiation to normal brain tissue is minimal. At the focal point, however, a very sizable dose is delivered which can, in certain cases, lead to obliteration of the lesion. This system has generally been quite expensive.

Although various of the prior designs and techniques have been useful in treating patients, there still are various problems. Treatment times are often relatively long. Further, matching up the radiation to a tumor or other target often has required complex algorithms. As discussed, radiation is often either applied in too low a dose for effectiveness on the target or too much radiation is applied to healthy tissue. Indeed, sometimes there is both too low a dose for effectiveness on the target and too much radiation is applied to healthy tissue. Scatter radiation is a problem with various systems. Some techniques have been quite expensive.

OBJECTS AND SUMMARY OF THE INVENTION

Accordingly, it is a primary object of the present invention to provide a new and improved method and system for radiation therapy.

A more specific object of the present invention is to provide multi-source radiation treatment.

A still further object of the present invention is to provide radiation treatment with reduced treatment times such that the chances of patient movement are reduced.

Yet another object of the present invention is to provide radiation treatment where the portion of applied radiation that is on a target is increased and the portion of the applied radiation on healthy tissue is reduced.

A further object of the invention is to avoid or minimize the problems in other techniques as noted above.

The present invention relates to a novel system and method for radiation delivery that improves the duty cycle to almost its theoretical limit. "Duty cycle" is defined as the ratio of useful radiation intensity incident on a patient to the total useful radiation intensity produced by the machine in a given time. The theoretical limit of duty cycle is unitary, i.e., 1.0, whereas a duty cycle in a typical IMRT is 0.25. The present invention provides a beam delivery system embodying an array that comprises multiple radiation sources. The radiation sources may either be miniature X-ray machines or isotope radiation devices depending upon the purpose of treatment. In current systems, Cobalt-60 source is the first choice. Each individual source contributes a dose to a small field segment on a patient. Since each source is capable of being individually moved in space, the multi-source machine (MSU) can provide spatially non-uniform beam intensity, i.e., intensity modulated beams depending on the distance between each source and the patient. Because multiple sources can move at the same time, beam delivery time is of much shorter durations than in conventional systems. Scatter radiation is also greatly reduced over that in conventional MLC because beam attenuation is relatively insignificant between source and patient.

BRIEF DESCRIPTION OF THE DRAWINGS

The above and other features of the present invention will be more apparent when the following detailed description is considered in conjunction with the accompanying drawings wherein like characters represent like parts and in which:

FIG. 3A is a simplified cross-sectional side view of a first grid or wall design with non-divergent beams according to the invention and corresponding to a cross-section of FIG. 2 along lines 3A, whereas

FIG. 4A is a simplified cross-sectional view of a second grid or wall design with divergent beams according to the invention, whereas

DETAILED DESCRIPTION OF THE INVENTION

Figure 1:
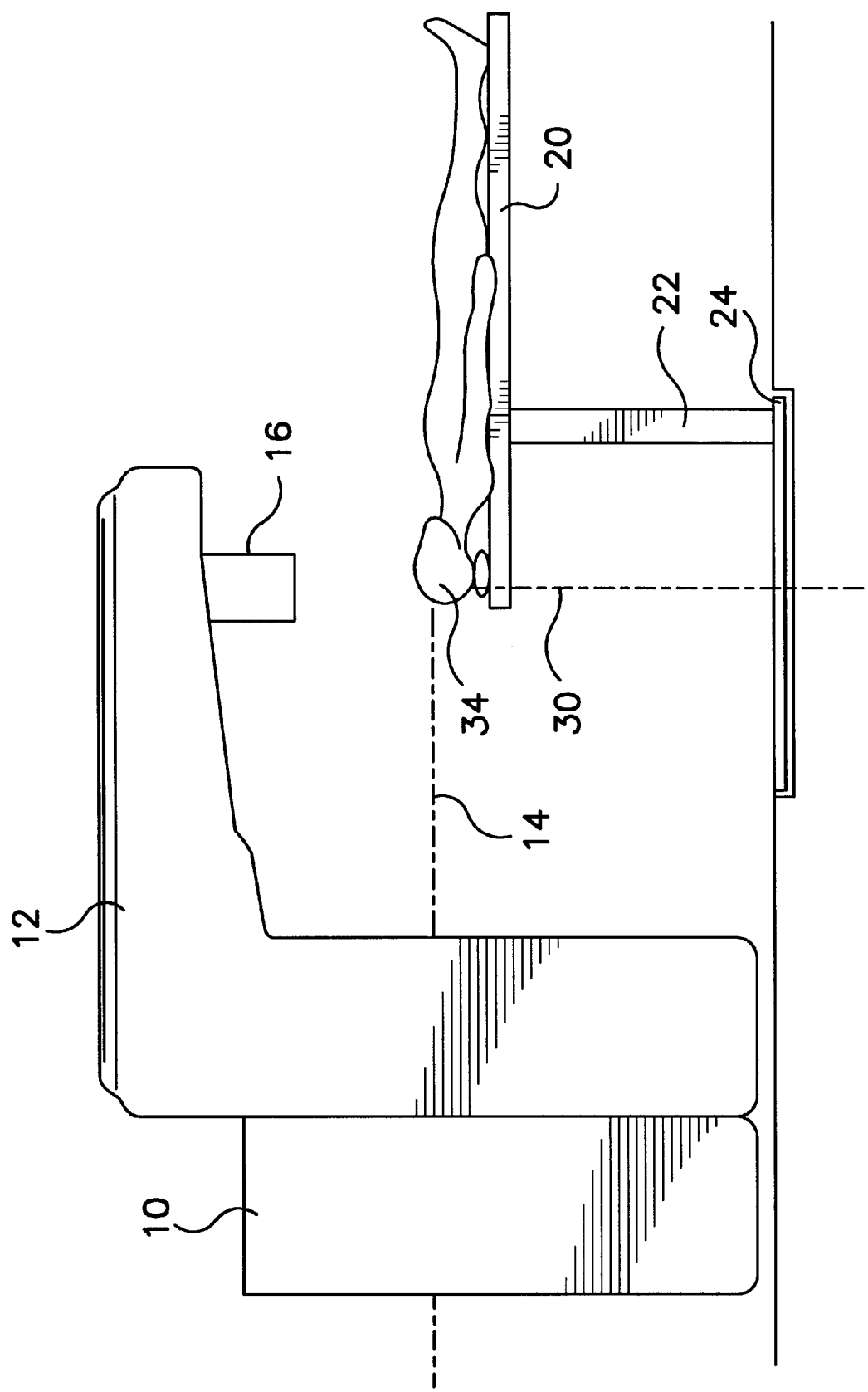
FIG. 1 is a side elevation view of a radiation therapy system embodying the invention.

FIG. 1 illustrates a radiation therapy or treatment setup with a patient on it.

Before explaining the array arrangement of the present invention in detail, the major components of FIG. 1 will be described briefly as most of the components are the same as in medical linear accelerator in general.

As shown, a patient is placed on a treatment table 20 that is supported by a member 22 on a rotating plate 24 positioned in the floor. Although not shown, constraints would secure the patient in position to the table. The radiation targeting shown in that figure corresponds to treatment of a brain tumor of the patient, but the present invention may also be used for treating tumors or other conditions in other parts of the body (i.e., parts other than the head). The rotating plate 24 may be rotated to position the table at different locations, thereby rotating the patient about a vertical axis 30. Gantry 12 may be rotated about base 10 to swing treatment array 16 in an arc located in a vertical plane, radiation at an isocenter or center point 34 corresponding to the intersection of the horizontal axis 14 of rotation of the gantry and a vertical plane in which axis 30 is disposed Center point 34 also corresponds to the origin of the arc through which the treatment head 16 swings. Rotating plate 24 rotates about a vertical axis which coincides with vertical plane 30. Accordingly, as gantry 12 is swung through an arc the radiation of head 16 passes through different portions of the patient's head and strikes center point 34 for all rotational positions of rotating plate 24.

Radiation therapy is used in approximately half of all cancer patients. The goal of such therapy is to uniformly deliver prescribed doses to the tumor volume while sparing the normal tissue. Intensity-Modulated Radiation Therapy (IMRT) has the potential to deliver the most conformal radiation to the tumor volume provided that the delivery system is optimally designed.

The MSU (multi-source unit) beam delivery system using head 16 of the present invention provides multiple radiation sources, e.g., cobalt-60. Each individual source contributes a dosage to a small segment of tumor volume. Radiation dose is inversely proportional to the square of the distance between the radiation source and the patient. Each source of MSU can individually move spatially (i.e., up and down). It is, therefore, very simple to provide an intensity-modulated radiation beam by placing sources at different distances from the patient.

The most widely used system for intensity-modulated radiation beam delivery is the multi-leaf collimator (MLC). This system suffers from two significant drawbacks. One is the treatment time and the other is unwanted total body irradiation due to increased leakage and scatter dose.

However, these drawbacks are completely obviated by the MSU system of the present invention. Beam delivery is much faster and efficient in a MSU system than an MLC system. The significant decreases in treatment times reduces the chance of possible patient movement during treatments, thereby increasing the accuracy of treatment. Scatter dose is also significantly reduced because there is no material blocking the beam pathway. Decreases in scatter and leakage dose are very important for minimizing side effects due to the irradiation of normal tissue.

The radiation therapy treatment system of the invention enables the provision of an intensity modulated radiation beam. The system of the invention also enables increased efficiency of intensity modulated radiation beam delivery while, at the same time, decreasing the potential of unnecessary and harmful scatter dose.

The design increases efficiency of intensity modulated radiation beam delivery. It also decreases unnecessary scatter and leakage dose that is potentially harmful for patients.

Figure 2:
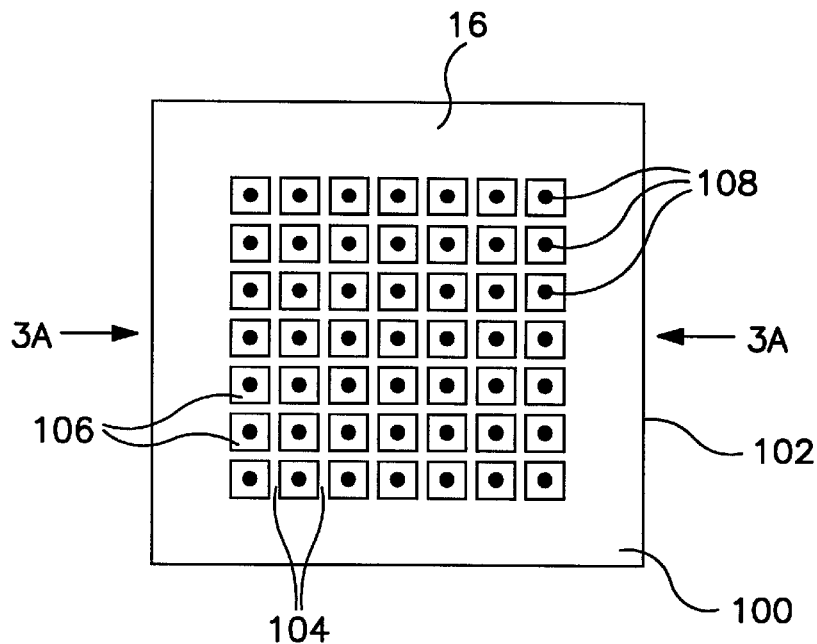
FIG. 2 is a planar view from the bottom of an array of radiation sources according to the present invention.

Turning to FIG. 2, the head 16 includes a mount 100 that is a grid with outer walls 102 and cell walls 104 made of radiation blocking material. Within cell walls 104 are cells 106 that have open space in which radiation sources 108, such as individual cobalt-60 sources, are disposed at the end of corresponding shafts or control rods 110. It will be understood in connection with FIG. 2 and the remaining figures that various components are identical to each other in the array and, for ease of illustration, only some of them are numbered. The mount supports, directly or indirectly, the sources 108. The number and dimensions of sources of radiation may vary depending upon the contemplated application.

Figure 3A:
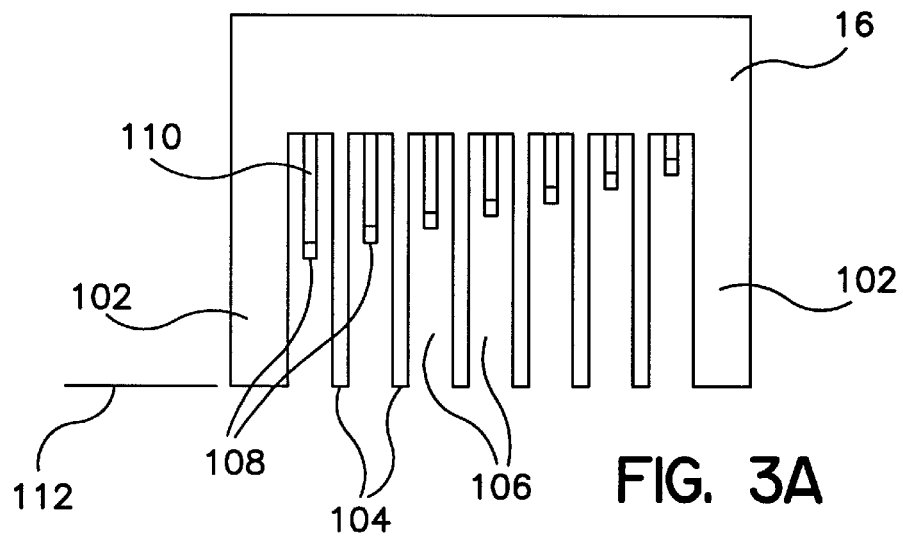

Turning now to FIG. 3A, the simplified cross-section view along lines 3A—3A of FIG. 2, the mount 16 provides a plurality of non-divergent beams from each of the sources 108. The beams are also non-convergent in that they are not focused at a point as are the beams in the GAMMA KNIFE arrangement. As shown, the sources 108 are at different vertical positions (i.e., relative to the view of FIG. 3A). As will be explained in detail below, the sources may be moved toward and away from a plane 112 at which the beams exit the mount or grid structure. The cell walls 104 are parallel as are the outer walls 102 (or at least those sides of the outer walls bounding a cell).

Figure 3B:
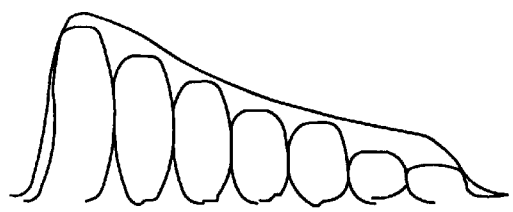
FIG. 3B shows radiation intensity corresponding to the portion of the grid directly above.

As shown just below FIG. 3A in FIG. 3B, the individual intensities of radiation from each source combine to an overall intensity that can be matched to the local properties of a target, such as characteristics or dimensions of that portion of a tumor subject to radiation from a given source at a given time. By moving the sources toward or away from the plane 112, and thus toward or away from a patient (not shown in FIGS. 3A and 3B), the intensity of radiation can be modulated to apply radiation to a target in a highly efficient manner.

Figure 4A:
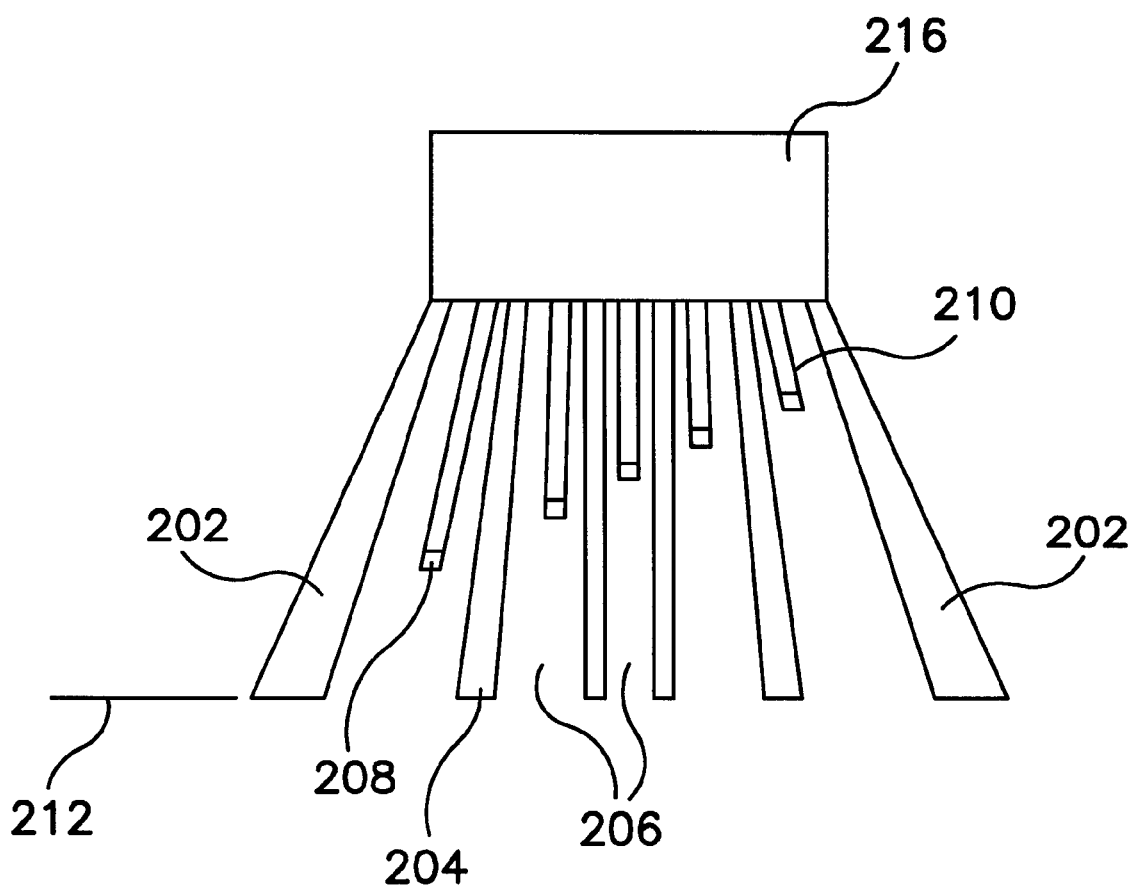

Turning now to FIG. 4A, a second embodiment has components in the "200" series with the same last two digits as the corresponding component, if any, in the FIG. 3A arrangement. The mount 216 provides a plurality of divergent beams from each of the sources 208. The beams are also non-convergent in that they are not focused at a point as are the beams in the GAMMA KNIFE arrangement. As shown, the sources 208 are at different vertical positions (i.e., relative to the view of FIG. 4A). As will be explained in detail below, the sources may be moved toward and away from a plane 212 at which the beams exit the mount or grid structure 216. The cell walls 204 are divergent as are the outer walls 102 (or at least those sides of the outer walls bounding a cell).

Figure 4B:
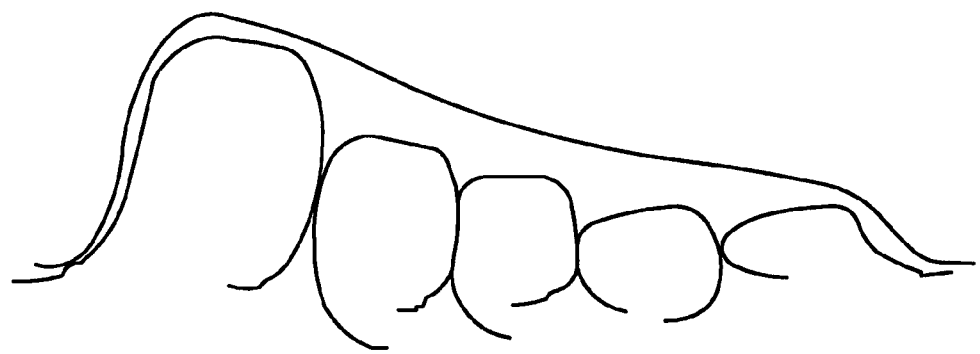
FIG. 4B shows radiation intensity corresponding to the portion of the grid directly above.

As shown just below FIG. 4A in FIG. 4B, the individual intensities of radiation from each source combine to an overall intensity that can be matched to the local properties of a target, such as characteristics or dimensions of that portion of a tumor subject to radiation from a given source at a given time. By moving the sources toward or away from the plane 212, and thus toward or away from a patient (not shown in FIGS. 4A and 4B), the intensity of radiation can be modulated to apply radiation to a target in a highly efficient manner.

Figure 5:
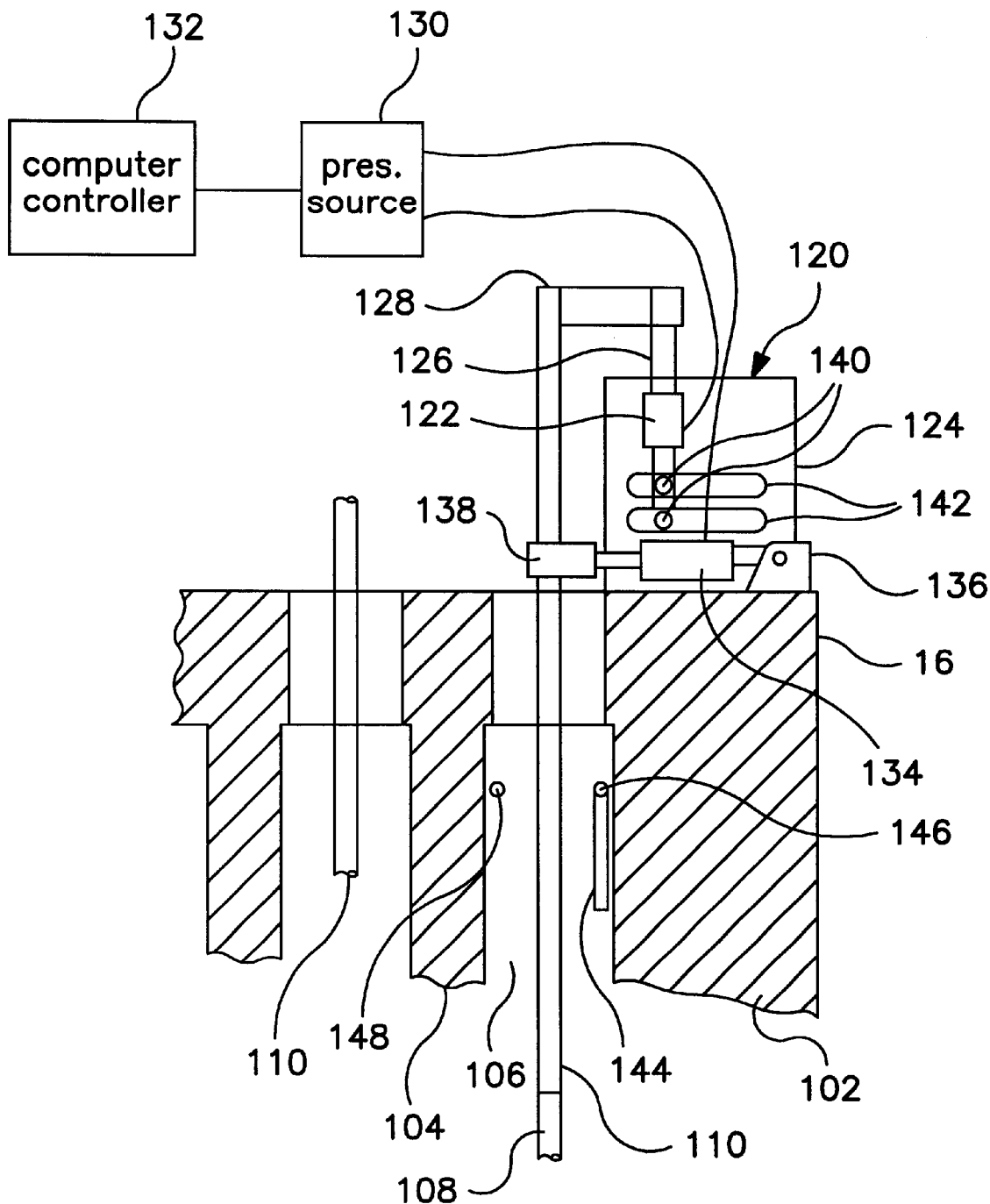
FIG. 5 is a simplified side view, with portions broken away and parts in cross-section of a portion of a grid structure and related parts and showing a source positioner arrangement used in the present invention.

Turning now to FIG. 5, and keeping in mind that the present invention is not limited to any particular technique for controlling the position of the various sources, the source 108 (only one shown in FIG. 5) may be moved within a cell 106 in a manner discussed here. A position controller 120 corresponding to each source 108 allows it to be moved within the corresponding cell 106. The illustrated position controller 120 serves as a source modulator in that movement of the source 108 allows one to increase or reduce the intensity of radiation applied to a patient.

Source positioner 120 most importantly includes an actuator such as double acting hydraulic cylinder 122 (with piston therein) having a lower end fixed against vertical movement to plate 124 on mount 16. A rod 126 of cylinder 122 is fixed to an upper end 128 of rod 110. A pressure source 130 extends and retracts cylinder 122 by hydraulic connections thereto as set by a controller 132 (such as a computer) according to a radiation therapy plan from an oncologist. This causes source 108 to move up and down (i.e., in the view of FIG. 5), down corresponding to an increased intensity of radiation applied to the patient and up corresponding to reduced intensity of radiation applied. This movement is determined based on the local properties of a target. This intensity modulation, accomplished by movement in the preferred embodiments, significantly allows beam modulation over a continuous range (as opposed to simply turning beams on and off).

In addition to the important movement toward and away from the patient supplied by cylinder 122, source positioner includes an optional feature using cylinder 134 (with piston therein) to provide movement right and left (i.e., in the view of FIG. 5) of source 108. Cylinder 134 has a left side fixed at two points on plate 136 attached to mount 16. The right side of cylinder 134 includes a ring 136 mounted on the rod end of the double acting cylinder. Rod 110 may slide up and down within ring 138 when cylinder 122 is extended or retracted.

Cylinder 122 may accommodate the right and left movement supplied to rod 110 by cylinder 134 by having its lower end pinned to slides 140 that can slide with corresponding parallel channels 142.

The source positioner 120 allows movement of the source 108 in two dimensions corresponding to vertical and horizontal directions in FIG. 5. However, one could alternately have the source movable in three dimensions.

The cell 106 may optionally have a hinged radiation blocking door 144 that pivots about axis 146 (perpendicular to the plane of view). The door 144 may be spring loaded to close to stop 148 when the source is retracted behind (i.e., above in FIG. 5) hinge axis 144. Alternately, the door can be computer controlled. By allowing an individual source 108 to be retracted behind a door 144, that source can, in effect, be turned off when appropriate for a given point in a scan.

FIG. 5 shows only one source positioner 120, but it will be readily understood that there would be a source positioner corresponding to each of the sources 108. Further, this same type of positioner with minor modifications, to account for the divergent pattern, could be used for the FIG. 4A arrangement of sources 208.

Although not shown in FIG. 5, the various position controlling cylinders 122 and 134 could have sensors to provide a closed feedback loop to maintain their accuracy. Moreover, the actuators 122 and 124 could be stepper motors or other electrical actuators, instead of the illustrated cylinders.

Although specific embodiments have been disclosed above, it will be understood that these are for illustrative purposes only. Various modifications and adaptations will be apparent to those of skill in the art. Therefore, the scope of the present invention will be determined by reference to the claims appended hereto.

What is claimed is:

1. A radiation therapy system comprising:
    an array of radiation sources, each having a corresponding beam;
    a mount supporting the array of radiation sources;
    a mount positioner operably connected to the mount for causing relative movement between the mount and a patient such that the mount is adjacent a patient being subjected to radiation from the array of radiation sources; and
    a plurality of source positioners, each connected to a corresponding one of the radiation sources and operable to move the corresponding radiation source toward and away from a patient such that the intensity of radiation is modulated dependent on the positions of the various radiation sources relative to a patient.
2. The radiation therapy system of claim 1 wherein the array extends in two orthogonal directions and the mount includes a grid of radiation-blocking walls with cells in between the walls, each radiation source disposed within a corresponding one of the cells, each source positioner operable to move the corresponding radiation source within its cell.

3. The radiation therapy system of claim 2 wherein the radiation sources are arranged such that the corresponding beams are non-converging.

4. The radiation therapy system of claim 3 wherein the walls are arranged such that the radiation sources have non-diverging beams.

5. The radiation therapy system of claim 3 wherein the walls are arranged such that the radiation sources have diverging beams.

6. The radiation therapy system of claim 3 wherein the walls of the grid define a plane from which all of the beams exit the grid and further comprising a controller operable to control the source positioners such that the positions of the various sources are individually moved toward and away from a patient depending on local properties of a target zone within a patient.

7. A radiation therapy system comprising:
   a two-dimensional array of radiation sources arranged within a grid defining a plane, the grid having walls between adjacent cells;
   a mount supporting the array of radiation sources, each having a corresponding beam; and
   a mount positioner operably connected to the mount for causing relative movement between the mount and a patient such that the mount is adjacent a patient being subjected to radiation from the array of radiation sources with the beams disposed across two orthogonal directions parallel to the plane, and wherein the radiation sources are arranged such that the corresponding beams are non-converging.

8. The radiation therapy system of claim 7 further comprising a plurality of source positioners, each connected to a corresponding one of the radiation sources and operable to move the corresponding radiation source toward and away from a patient such that the intensity of radiation is modulated dependent on the positions of the various radiation sources relative to a patient.

9. The radiation therapy system of claim 8 further comprising a controller operable to control the source positioners such that the positions of the various sources are individually moved toward and away from a patient depending on local properties of a target zone within a patient.

10. The radiation therapy system of claim 9 wherein the plane defined by the grid is a plane from which all of the beams exit the grid.

11. The radiation therapy system of claim 9 wherein each radiation sources is radioactive material.

12. The radiation therapy system of claim 8 wherein each source positioner is operable to modulate radiation intensity applied to a patient from the corresponding radiation source over a continuous range.

13. A radiation therapy system comprising:
    an array of radiation sources;
    a mount supporting the array of radiation sources;
    a mount positioner operably connected to the mount for causing relative movement between the mount and a patient such that the mount is adjacent a patient being subjected to radiation from the array of radiation sources; and
    a plurality of source modulators, each operable to modulate radiation intensity over a continuous range and from a corresponding one of the radiation sources as applied to a patient.

14. The radiation therapy system of claim 13 wherein the array extends in two orthogonal directions and the mount includes a grid of radiation-blocking walls with cells in between the walls, each radiation source disposed within a corresponding one of the cells.

15. The radiation therapy system of claim 14 wherein each source modulator is a source positioner operable to modulate radiation applied to a patient by moving the corresponding source toward or away from a patient.

16. The radiation therapy system of claim 15 wherein the walls and the radiation sources are arranged such that the corresponding beams are non-converging.

17. The radiation therapy system of claim 16 further comprising a controller operable to control the source positioners such that the positions of the various sources are individually moved toward and away from a patient depending on local properties of a target zone within a patient.

18. The radiation therapy system of claim 13 wherein the radiation sources are arranged such that the corresponding beams are non-converging.

19. A method of applying radiation therapy to a patient, the steps comprising:
    providing an array of radiation sources;
    causing relative movement between the array of radiation sources and a patient such that the array of radiation sources is adjacent the patient and the patient is subjected to radiation from the array of radiation sources; and
    individually modulating radiation intensity from each of the radiation sources in the array of radiation sources and over a continuous range, and wherein the continuous range modulation of provides three-dimensional conformal radiation therapy.

20. The method of claim 19 wherein the modulating of the radiation intensity of each of the radiation sources is dependent on local properties of a target zone within a patient.

21. The method of claim 20 wherein each of the radiation sources provides a corresponding beam and wherein the beams are non-converging.

22. The method of claim 21 wherein the beams are non-diverging.

23. The method of claim 21 wherein the beams are diverging.

24. The method of claim 21 wherein the step of individually modulating radiation intensity from each of the radiation sources is accomplished by using a plurality of source positioners, each moving the corresponding radiation source towards or away from a patient.

* * * * *